United States Patent
Michalak et al.

(10) Patent No.: US 8,399,631 B2
(45) Date of Patent: Mar. 19, 2013

(54) COMPOSITIONS AND METHODS FOR PURIFYING CALRETICULIN

(75) Inventors: Marek Michalak, Edmonton (CA); Monika Dabroska, Edmonton (CA)

(73) Assignee: Calretex LLC, New York, NY (US)

( * ) Notice: Subject to any disclaimer, the term of this patent is extended or adjusted under 35 U.S.C. 154(b) by 38 days.

(21) Appl. No.: 12/557,818

(22) Filed: Sep. 11, 2009

(65) Prior Publication Data

US 2010/0145016 A1    Jun. 10, 2010

Related U.S. Application Data

(60) Provisional application No. 61/096,185, filed on Sep. 11, 2008.

(51) Int. Cl.
| | |
|---|---|
| C12N 15/00 | (2006.01) |
| C12N 15/12 | (2006.01) |
| C12N 1/21 | (2006.01) |
| C07B 63/00 | (2006.01) |
| G01N 30/00 | (2006.01) |

(52) U.S. Cl. ....... 530/412; 530/416; 530/417; 435/69.1; 435/320.1; 435/252.3; 435/252.33

(58) Field of Classification Search ................ None
See application file for complete search history.

(56) References Cited

U.S. PATENT DOCUMENTS

| | | | |
|---|---|---|---|
| 6,171,864 B1 * | 1/2001 | Coughlan et al. | 435/469 |
| 2004/0248217 A1 * | 12/2004 | Yoshiki et al. | 435/7.23 |
| 2005/0054820 A1 * | 3/2005 | Wu et al. | 530/350 |

OTHER PUBLICATIONS

Novagen, TB026, Dec. 1998, "pET-3a-d Vectors." pp. 1-2.*
GenBank Accession No. AD000092, accessed May 17, 2011, "*Homo sapiens* DNA from chromosome 19p13.2 cosmids R—Nucleotide result", pp. 1-40.*
Baksh et al., 1991, J. Biol. Chem. 266:21458-21465.*
Milner et al., 1991, J. Biol. Chem. 266:7155-7165.*

* cited by examiner

*Primary Examiner* — Elizabeth C Kemmerer
(74) *Attorney, Agent, or Firm* — Fish & Richardson P.C.

(57) ABSTRACT

The present invention relates to compositions, methods for expressing, and related methods for purifying calreticulin that is free of an affinity label or tag (i.e., non-tagged calreticulin). The invention provides useful methods for commercial production of human calreticulin in a bacterial expression system such as *Escherichia coli*.

14 Claims, 9 Drawing Sheets

FIGURES 3A-D 7.5 µg   15 µg   30 µg   of purified hCRT

FIGURE 6A

AAGAAACCAATTGTCCATATTGCATCAGACATTGCCGTCACTGCGTCTTTTACTGGCTCTTC
TCGCTAACCAAACCCGTAACCCCCGCTTATTAAAAGCATTCTGTAACAAAGCCGGTACCAAAGC
CATGACAAAAACGCGTAACAAAAGTGTCTATAATCACGGCAGAAAAGTCCACATTGATTATT

<sub>GL96-seq F</sub>  <sub>BamHI (239)</sub>
TGCACGGCGTCACACTTTGCTATGCCATAGCATTTTTATCCTTAAGATTAGCCGATCCTACC
TTACGGTTTTTATCGCAACTCTCTACTGTTTCTCCATACCCGTTTTTTGGGCTAACACGACGG
AATTAACCATGAAAAAACTGCTGTTCGCCATTCCCCTGGTGGTGCCGTTCTATAGCCATAGC
▸ M K K L L F A I P L V V P F Y S H S <sub>SacI (383)   junction marker (387)</sub>
<sub>NcoI (374)  XhoI (382)</sub>

ACCATGGAGCTCGAG gagctgccg tctacttcaa ggagcagttt ctggacggag
▸ T M E L E E P A V Y F K E Q F L D G acgggtggac ttcccgctgg atcgaatcca aacacaagtc agattttggc
▸ D G W T S R W I E S K H K S D F G aaattcgttc tcagttccgg caagttctac ggtgacgagg agaaagataa
▸ K F V L S S G K F Y G D E E K D K aggtttgcag acaagccagg atgcacgctt ttatgctctg tggccagtt
▸ G L Q T S Q D A R F Y A L S A S tcgagccttt cagcaacaaa ggccagagc tgtggtgca gttcacggtg
▸ F E P F S N K G Q T L V V Q F T V aaacatgagc agaacatcga ctgtgggggc ggctatgtga agctgttcc
▸ K H E Q N I D C G G G Y V K L F P taatagtttg gaccagacag acatgcacgg agactcagaa tacaacatca
▸ N S L D Q T D M H G D S E Y N I tgttttggtcc cgacatctgt ggccctggca ccaagaaggt tcatgtcatc
▸ M F G P D I C G P G T K K V H V I ttcaactaca agggcaagaa cgtgctgatc aacaaggaca tccgttgcaa
▸ F N Y K G K N V L I N K D I R C K ggatgatgag ttaacacacc tgtacacact gattgtgcgg ccagacaaca
▸ D D E F T H L Y T L I V R P D N cctatgaggt gaagattgac aacagccagg tggagtccgg ctccttggaa
▸ T Y E V K I D N S Q V E S G S L E gacgattggg acttcctgcc accaaagaag ataaaggatc ctgatgctta
▸ D D W D F L P P K K I K D P D A S aaaaccggaa gactgggatg agcgggccaa gatcgatgat cccacagact
▸ K P E D W D E R A K I D D P T D ccaagcctga ggactggaca aagccgagc atatccctga ccctgatgct
▸ S K P E D W D K P E H I P D P D A <sub>YQ15-seq.R (1101)</sub>
aagaagccg aggactggga tgaagagatg gacggagagt ggaagccccc
▸ K K P E D W D E E M D G E W E P P agtgattcag aaccctgagt acaagggtga gtggaagccc ggcagatca
▸ V I Q N P E Y K G E W K P R Q I acaacccaga ttacaagggc acttggatcc accagaaaat tgacaacccc
▸ D N P D Y K G T W I H P E I D N P

FIGURE 6B

```
gagtattctc ccgatcccag tatctatgcc tatgataact ttgggtgct
 E   Y   S    P   D   P   S    I   Y   A    Y   D   N    F   G   V   L
gggcctggac atctggcagg tcaagtctgg caccatcttt gacaacttcc
 G   L   D    L   W   Q    V   K   S    G   T   I   F    D   N   F
tcatcaccaa cgatgaggca tacgctgagg agtttggcaa cgagacgtgg
 L   I   T   N    D   E   A    Y   A   E    E   F   G   N    E   T   W
ggcgtaacaa aggcagcaga gaaacaaatg aaggacaaac aggacgagga
 G   V   T   K    A   A   E    K   Q   M    K   D   K    Q   D   E   E
gcagaggctt aaggaggagg aagaagacaa gaaacgcaaa gaggaggagg
 Q   R   L    K   E   E    E   E   D   K    K   R   K    E   E   E
aggcagagga caaggaggat gatgaggaca agatgaggga tgaggaggat
 A   E   D    K   E   D    D   E   D    K   D   E    E   D
gaggaggaca aggaggaaga tgaggaggaa gatgtccccg gccaggccaa
 E   E   D    K   E   E    E   E   D    V   P   G   Q   A   K
                                                    XbaI (1604)
                                     HindIII (1598)
ggacgagctg TAGgaattc GAAGCTTTCTAGAACAAAAACTCATCTCAGAAGAGGATCTG
 D   E   L
           SalI (1647)
AATAGCGCCGTCGACCATCATCATCATCATCATTGAGTTTAAACGGTCTCCAGCTTGCTGCT
           XmnI (1718)              GL97-seq.R
TTTGGCCGATGAGAGAAGATTTTCAGCCTGATACAGATTAAATCAGAACGGCAGAAGCGGTCT
GATAAAACAGAATTTGCCTGGCGGCAGTAGCGCGGTGGTCCCACCTGACCCCATGCCGAACT
CAGAAGTGAAACGCCGTAGCGCCGATGGTAGTGTGGGGTCTCCCCATGCGAGAGTAGGGAAC
TGCCAGGCATCAAATAAAACGAAAGGCTCAGTCGAAAGACTGGGCCTTTCCTTTTATCTTTT
GTTTGTCGGTGAACGCTCTCCTGAGTAGGACAAATCGGCCGGGAGCCGATTTGAACGTTGCG
AAGCAACGGCCCGGAGGGTGGCGGGCAGGACGCCCGCCATAAACTGCCAGGCATCAAATTAA
GCAGAAGGCCATCCTGACGGATGGCCTTTTTGCGTTTCTACAAACTCTTTTTGTTTATTTTTT
CTAAATACATTCAAATATGTATCCGCTCATGAGACAATAACCCTGATAAATGCTTCAATAAT
ATTGAAAAAGGAAGAGTATGAGTATTCAACATTTCCGTGTCGCCCTTATTCCCTTTTTTGCG
GCATTTTGCCTTCCTGTTTTTGCTCACCCAGAAACGCTGGTGAAAGTAAAAGATGCTGAAGA
TCAGTTGGGTGCACGAGTGGGTTACATCGAACTGGATCTCAACAGCGGTAAGATCCTTGAGA
           XmnI (2400)
GTTTTCGCCCCGAAGAACGTTTTCCAATGATGAGCACTTTTAAAGTTCTGCTATGTGGCGCG
GTATTATCCCGTGTTGACGCCGGGCAAGAGCAACTCGGTCGCCGCATACACTATTCTCAGAA
           ScaI (2518)
TGACTTGGTTGAGTACTCACCAGTCACAGAAAAGCATCTTACGGATGGCATGACAGTAAGAG
AATTATGCAGTGCTGCCATAACCATGAGTGATAACACTGCGGCCAACTTACTTCTGACAACG
ATCGGAGGACCGAAGGAGCTAACCGCTTTTTTGCACAACATGGGGGATCATGTAACTCGCCT
TGATCGTTGGGAACCGGAGCTGAATGAAGCCATACCAAACGACGAGCGTGACACCACGATGC
CTGTAGCAATGGCAACAACGTTGCGCAAACTATTAACTGGCGAACTACTTACTCTAGCTTCC
CGGCAACAATTAATAGACTGGATGGAGGCGGATAAAGTTGCAGGACCACTTCTGCGCTCGGC
CCTTCCGGCTGGCTGGTTTATTGCTGATAAATCTGGAGCCGGTGAGCGTGGGTCTCGCGGTA
TCATTGCAGCACTGGGGCCAGATGGTAAGCCCTCCCGTATCGTAGTTATCTACACGACGGGG
```

FIGURE 6C

AGTCAGGCAACTATGGATGAACGAAATAGACAGATCGCTGAGATAGGTGCCTCACTGATTAA
GCATTGGTAACTGTCAGACCAAGTTTACTCATATATACTTTAGATTGATTTAAAACTTCATT
TTTAATTTAAAAGGATCTAGGTGAAGATCCTTTTTGATAATCTCATGACCAAAATCCCTTAA
CGTGAGTTTTCGTTCCACTGAGCGTCAGACCCCGTAGAAAAGATCAAAGGATCTTCTTGAGA
TCCTTTTTTTCTGCGCGTAATCTGCTGCTTGCAAACAAAAAAACCACCGCTACCAGCGGTGG
TTTGTTTGCCGGATCAAGAGCTACCAACTCTTTTTCCGAAGGTAACTGGCTTCAGCAGAGCG
CAGATACCAAATACTGTCCTTCTAGTGTAGCCGTAGTTAGGCCACCACTTCAAGAACTCTGT
AGCACCGCCTACATACCTCGCTCTGCTAATCCTGTTACCAGTGGCTGCTGCCAGTGGCGATA
AGTCGTGTCTTACCGGGTTGGACTCAAGACGATAGTTACCGGATAAGGCGCAGCGGTCGGGC
TGAACGGGGGGTTCGTGCACACAGCCCAGCTTGGAGCGAACGACCTACACCGAACTGAGATA
CCTACAGCGTGAGCTATGAGAAAGCGCCACGCTTCCCGAAGGGAGAAAGGCGGACAGGTATC
CGGTAAGCGGCAGGGTCGGAACAGGAGAGCGCACGAGGGAGCTTCCAGGGGGAAACGCCTGG
TATCTTTATAGTCCTGTCGGGTTTCGCCACCTCTGACTTGAGCGTCGATTTTTGTGATGCTC
GTCAGGGGGGCGGAGCCTATGGAAAAACGCCAGCAACGCGGCCTTTTTACGGTTCCTGGCCT
TTTGCTGGCCTTTTGCTCACATGTTCTTTCCTGCGTTATCCCCTGATTCTGTGGATAACCGT
ATTACCGCCTTTGAGTGAGCTGATACCGCTCGCCGCAGCCGAACGACCGAGCGCAGCGAGTC
AGTGAGCGAGGAAGCGGAAGAGCGCCCTGATGCGGTATTTTCTCCTTACGCATCTGTGCGGTA
<br>Ndel (4067)
TTTCACACCGCATATGGTGCACTCTCAGTACAATCTGCTCTGATGCCGCATAGTTAAGCCAG
TATACACTCCGCTATCGCTACGTGACTGGGTCATGGCTGCGCCCCGACACCCGCCAACACCC
GCTGACGCGCCCTGACGGGCTTGTCTGCTCCCGGCATCCGCTTACAGACAAGCTGTGACCGT
CTCCGGGAGCTGCATGTGTCAGAGGTTTTCACCGTCATCACCGAAACGCGCGAGGCAGCAGA
<br>SphI (4333)
TCAATTCGCGCGCGAAGGCGAAGCGGCATGCATAATGTGCCTGTCAAATGGACGAAGCAGGG
ATTCTGCAAACCCTATGCTACTCCGTCAAGCCGTCAATTGTCTGATTCGTTACCAATTATGA
CAACTTGACGGCTACATCATTCACTTTTTCTTCACAACCGGCACGGAACTCGCTCGGGCTGG
CCCCGGTGCATTTTTTAAATACCCGCGAGAAATAGAGTTGATCGTCAAAACCAACATTGCGA
CCGACGGTGGCGATAGGCATCCGGGTGGTGCTCAAAAGCAGCTTCGCCTGGCTGATACGTTG
GTCCTCGCGCCAGCTTAAGACGCTAATCCCTAACTGCTGGCGGAAAAGATGTGACAGACGCG
<br>EcoRV (4712)
ACGGCGACAAGCAAACATGCTGTGCGACGCTGGCGATATCAAAATTGCTGTCTGCCAGGTGA
TCGCTGATGTACTGACAAGCCTCGCGTACCCGATTATCCATCGGTGGATGGAGCGACTCGTT
AATCGCTTCCATGCGCCGCAGTAACAATTGCTCAAGCAGATTTATCGCCAGCAGCTCCGAAT
AGCGCCCTTCCCCTTGCCCGGCGTTAATGATTTGCCCAAACAGGTCGCTGAAATGCGGCTGG
TGCGCTTCATCCGGGCGAAAGAACCCCGTATTGGCAAATATTGACGGCCAGTTAAGCCATTC
ATGCCAGTAGGCGCGCGGACGAAAGTAAACCCACTGGTGATACCATTCGCGAGCCTCCGGAT
GACGACCGTAGTGATGAATCTCTCCTGGCGGGAACAGCAAAATATCACCCGGTCGGCAAACA
AATTCTCGTCCCTGATTTTTCACCACCCCCTGACCGCGAATGGTGAGATTGAGAATATAACC
TTTCATTCCCAGCGGTCGGTCGATAAAAAAATCGAGATAACCGTTGGCCTCAATCGGCGTTA
AACCCGCCACCAGATGGCATTAAACGAGTATCCCGGCAGCAGGGGATCATTTTGCGCTTCA

FIGURE 6 D

GCCATACTTTTCATACTCCCGCCATTCAGAG   junction marker

SEQUENCE LISTING

```
<160> NUMBER OF SEQ ID NOS: 13

<210> SEQ ID NO 1
<211> LENGTH: 24
<212> TYPE: DNA
<213> ORGANISM: artificial sequence
<220> FEATURE:
<223> OTHER INFORMATION: primer

<400> SEQUENCE: 1
atactcgagg agcctgccgt ctac                                          24

<210> SEQ ID NO 2
<211> LENGTH: 22
<212> TYPE: DNA
<213> ORGANISM: artificial sequence
<220> FEATURE:
<223> OTHER INFORMATION: primer

<400> SEQUENCE: 2
agggaattcc tacagctcgt cc                                            22

<210> SEQ ID NO 3
<211> LENGTH: 1899
<212> TYPE: DNA
<213> ORGANISM: Homo sapiens

<400> SEQUENCE: 3
gtccgtactg cagagccgct gccggagggt cgttttaaag ggccgcgttg ccgcccctc     60 ggcccgccat gctgctatcc gtgccgctgc tgctcggcct cctcggcctg gccgtcgccg    120
agcccgccgt ctacttcaag gagcagtttc tggacggaga cgggtggact tcccgctgga    180
tcgaatccaa acacaagtca gattttggca aattcgttct cagttccggc aagttctacg    240
gtgacgagga gaaagataaa ggtttgcaga caagccagga tgcacgcttt tatgctctgt    300
cggccagttt cgagcctttc agcaacaaag gccagacgct ggtggtgcag ttcacggtga    360
aacatgagca gaacatcgac tgtggggggcg gctatgtgaa gctgtttcct aatagtttgg    420
accagacaga catgcacgga gactcagaat acaacatcat gtttggtccc gacatctgtg    480
gccctggcac caagaaggtt catgtcatct tcaactacaa gggcaagaac gtgctgatca    540
acaaggacat ccgttgcaag gatgatgagt ttacacacct gtacacactg attgtgcggc    600
cagacaacac ctatgaggtg aagattgaca acagccaggt ggagtccggc tccttggaag    660
```

```
acgattggga cttcctgcca cccaagaaga taaaggatcc tgatgcttca aaaccggaag    720
actgggatga gcgggccaag atcgatgatc ccacagactc caagcctgag gactgggaca    780
agcccgagca tatccctgac cctgatgcta agaagcccga ggactgggat gaagagatgg    840
acggagagtg ggaaccccca gtgattcaga accctgagta caagggtgag tggaagcccc    900
ggcagatcga caacccagat tacaagggca cttggatcca cccagaaatt gacaaccccg    960
agtattctcc cgatcccagt atctatgcct atgataactt tggcgtgctg ggcctggacc   1020
tctggcaggt caagtctggc accatctttg acaacttcct catcaccaac gatgaggcat   1080
acgctgagga gtttggcaac gagacgtggg gcgtaacaaa ggcagcagag aaacaaatga   1140
aggacaaaca ggacgaggag cagaggctta aggaggagga agaagacaag aaacgcaaag   1200
aggaggagga ggcagaggac aaggaggatg atgaggacaa agatgaggat gaggaggatg   1260
aggaggacaa ggaggaagat gaggaggaag atgtccccgg ccaggccaag gacgagctgt   1320
agagaggcct gcctccaggg ctggactgag gcctgagcgc tcctgccgca gagcttgccg   1380
cgccaaataa tgtctctgtg agactcgaga actttcattt ttttccaggc tggttcggat   1440
ttggggtgga ttttggtttt gttcccctcc tccactctcc cccacccct ccccgccctt    1500
tttttttttt tttttaaact ggtattttat cctttgattc tccttcagcc ctcacccctg   1560
gttctcatct ttcttgatca acatcttttc ttgcctctgt gccccttctc tcatctctta   1620
gctcccctcc aacctggggg gcagtggtgt ggagaagcca caggcctgag atttcatctg   1680
ctctccttcc tggagcccag aggagggcag cagaagggg tggtgtctcc aaccccccag    1740
cactgaggaa gaacggggct cttctcattt caccctccc tttctcccct gccccagga     1800
ctgggccact tctgggtggg gcagtgggtc ccagattggc tcacactgag aatgtaagaa   1860
ctacaaacaa aatttctatt aaattaaatt ttgtgtctc                          1899
```

<210> SEQ ID NO 4
<211> LENGTH: 417
<212> TYPE: PRT
<213> ORGANISM: Homo sapiens

<400> SEQUENCE: 4

```
Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp Gly
            20                  25                  30

Trp Thr Ser Arg Trp Ile Glu Ser Lys His Lys Ser Asp Phe Gly Lys
        35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Asn Ser Leu Asp Gln Thr Asp Met His Gly Asp Ser Glu Tyr
        115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
145                 150                 155                 160
```

```
Ile Arg Cys Lys Asp Asp Glu Phe Thr His Leu Tyr Thr Leu Ile Val
            165                 170                 175
Arg Pro Asp Asn Thr Tyr Glu Val Lys Ile Asp Asn Ser Gln Val Glu
        180                 185                 190
Ser Gly Ser Leu Glu Asp Asp Trp Asp Phe Leu Pro Pro Lys Lys Ile
    195                 200                 205
Lys Asp Pro Asp Ala Ser Lys Pro Glu Asp Trp Asp Glu Arg Ala Lys
210                 215                 220
Ile Asp Asp Pro Thr Asp Ser Lys Pro Glu Asp Trp Asp Lys Pro Glu
225                 230                 235                 240
His Ile Pro Asp Pro Asp Ala Lys Lys Pro Glu Asp Trp Asp Glu Glu
                245                 250                 255
Met Asp Gly Glu Trp Glu Pro Pro Val Ile Gln Asn Pro Glu Tyr Lys
            260                 265                 270
Gly Glu Trp Lys Pro Arg Gln Ile Asp Asn Pro Asp Tyr Lys Gly Thr
        275                 280                 285
Trp Ile His Pro Glu Ile Asp Asn Pro Glu Tyr Ser Pro Asp Pro Ser
    290                 295                 300
Ile Tyr Ala Tyr Asp Asn Phe Gly Val Leu Gly Leu Asp Leu Trp Gln
305                 310                 315                 320
Val Lys Ser Gly Thr Ile Phe Asp Asn Phe Leu Ile Thr Asn Asp Glu
                325                 330                 335
Ala Tyr Ala Glu Glu Phe Gly Asn Glu Thr Trp Gly Val Thr Lys Ala
            340                 345                 350
Ala Glu Lys Gln Met Lys Asp Lys Gln Asp Glu Glu Gln Arg Leu Lys
        355                 360                 365
Glu Glu Glu Glu Asp Lys Lys Arg Lys Glu Glu Glu Ala Glu Asp
    370                 375                 380
Lys Glu Asp Asp Glu Asp Lys Asp Glu Asp Glu Asp Glu Asp Glu Asp
385                 390                 395                 400
Lys Glu Glu Asp Glu Glu Asp Val Pro Gly Gln Ala Lys Asp Glu
                405                 410                 415
Leu
```

<210> SEQ ID NO 5
<211> LENGTH: 7
<212> TYPE: PRT
<213> ORGANISM: artificial sequence
<220> FEATURE:
<223> OTHER INFORMATION: synthetic peptide

<400> SEQUENCE: 5

Lys Leu Gly Phe Phe Lys Arg
1               5

<210> SEQ ID NO 6
<211> LENGTH: 5326
<212> TYPE: DNA
<213> ORGANISM: Homo sapiens

<400> SEQUENCE: 6
aagaaaccaa ttgtccatat tgcatcagac attgccgtca ctgcgtcttt tactggctct    60
tctcgctaac caaaccggta accccgctta ttaaaagcat tctgtaacaa agcgggacca   120
aagccatgac aaaaacgcgt aacaaaagtg tctataatca cggcagaaaa gtccacattg   180
attatttgca cggcgtcaca ctttgctatg ccatagcatt tttatccata agattagcgg   240
atcctacctg acgcttttta tcgcaactct ctactgtttc tccatacccg ttttttgggc   300

```
taacaggagg aattaaccat gaaaaaactg ctgttcgcga ttccgctggt ggtgccgttc    360
tatagccata gcaccatgga gctcgaggag cctgccgtct acttcaagga gcagtttctg    420
gacggagacg ggtggacttc ccgctggatc gaatccaaac acaagtcaga ttttggcaaa    480
ttcgttctca gttccggcaa gttctacggt gacgaggaga agataaagg tttgcagaca    540 agccaggatg cacgctttta tgctctgtcg gccagtttcg agcctttcag caacaaaggc    600
cagacgctgg tggtgcagtt cacggtgaaa catgagcaga acatcgactg tggggcggc    660 tatgtgaagc tgtttcctaa tagtttggac cagacagaca tgcacggaga ctcagaatac    720
aacatcatgt ttggtcccga catctgtggc cctggcacca agaaggttca tgtcatcttc    780
aactacaagg gcaagaacgt gctgatcaac aaggacatcc gttgcaagga tgatgagttt    840
acacacctgt acacactgat tgtgcggcca gacaacacct atgaggtgaa gattgacaac    900
agccaggtgg agtccggctc cttggaagac gattgggact tcctgccacc caagaagata    960
aaggatcctg atgcttcaaa accggaagac tgggatgagc gggccaagat cgatgatccc   1020
acagactcca gcctgagga ctgggacaag cccgagcata tccctgaccc tgatgctaag   1080
aagcccgagg actgggatga agagatggac ggagagtggg aacccccagt gattcagaac   1140
cctgagtaca agggtgagtg gaagccccgg cagatcgaca acccagatta caagggcact   1200
tggatccacc cagaaattga caaccccgag tattctcccg atcccagtat ctatgcctat   1260
gataactttg gcgtgctggg cctggacctc tggcaggtca gtctggcac catctttgac   1320 aacttcctca tcaccaacga tgaggcatac gctgaggagt ttggcaacga gacgtggggc   1380
gtaacaaagg cagcagagaa acaaatgaag gacaaacagg acgaggagca gaggcttaag   1440
gaggaggaag aagacaagaa acgcaaagag gaggaggagg cagaggacaa ggaggatgat   1500
gaggacaaag atgaggatga ggaggatgag gaggacaagg aggaagatga ggaggaagat   1560
gtccccggcc aggccaagga cgagctgtag gaattcgaag ctttctagaa caaaaactca   1620
tctcagaaga ggatctgaat agcgccgtcg accatcatca tcatcatcat tgagtttaaa   1680
cggtctccag cttggctgtt ttggcggatg agaagagatt ttcagcctga tacagattaa   1740
atcagaacgc agaagcggtc tgataaaaca gaatttgcct ggcggcagta gcgcggtggt   1800
cccacctgac cccatgccga actcagaagt gaaacgccgt agcgccgatg gtagtgtggg   1860
gtctccccat gcgagagtag ggaactgcca ggcatcaaat aaaacgaaag gctcagtcga   1920
aagactgggc ctttcgtttt atctgttgtt tgtcggtgaa cgctctcctg agtaggacaa   1980
atccgccggg agcggatttg aacgttgcga agcaacggcc cggagggtgg cgggcaggac   2040
gcccgccata aactgccagg catcaaatta agcagaaggc catcctgacg gatggccttt   2100
ttgcgtttct acaaactctt tttgtttatt tttctaaata cattcaaata tgtatccgct   2160
catgagacaa taaccctgat aaatgcttca ataatattga aaaggaaga gtatgagtat   2220 tcaacatttc cgtgtcgccc ttattccctt ttttgcggca ttttgccttc ctgtttttgc   2280
tcacccagaa acgctggtga agtaaaaga tgctgaagat cagttgggtg cacgagtggg   2340
ttacatcgaa ctggatctca acagcggtaa gatccttgag agttttcgcc ccgaagaacg   2400
ttttccaatg atgagcactt taaagttct gctatgtggc gcggtattat cccgtgttga   2460
cgccgggcaa gagcaactcg gtcgccgcat acactattct cagaatgact tggttgagta   2520
ctcaccagtc acagaaaagc atcttacgga tggcatgaca gtaagagaat tatgcagtgc   2580
tgccataacc atgagtgata acactgcggc caacttactt ctgacaacga tcggaggacc   2640
gaaggagcta accgcttttt tgcacaacat gggggatcat gtaactcgcc ttgatcgttg   2700
```

```
ggaaccggag ctgaatgaag ccataccaaa cgacgagcgt gacaccacga tgcctgtagc    2760
aatggcaaca acgttgcgca aactattaac tggcgaacta cttactctag cttcccggca    2820
acaattaata gactggatgg aggcggataa agttgcagga ccacttctgc gctcggccct    2880
tccggctggc tggtttattg ctgataaatc tggagccggt gagcgtgggt ctcgcggtat    2940
cattgcagca ctgggccag atggtaagcc ctcccgtatc gtagttatct acacgacggg    3000
gagtcaggca actatggatg aacgaaatag acagatcgct gagataggtg cctcactgat    3060
taagcattgg taactgtcag accaagttta ctcatatata ctttagattg atttaaaact    3120 tcattttaa tttaaaagga tctaggtgaa gatccttttt gataatctca tgaccaaaat    3180
cccttaacgt gagttttcgt tccactgagc gtcagacccc gtagaaaaga tcaaaggatc    3240
ttcttgagat cctttttttc tgcgcgtaat ctgctgcttg caaacaaaaa aaccaccgct    3300
accagcggtg gtttgtttgc cggatcaaga gctaccaact cttttccga aggtaactgg    3360 cttcagcaga gcgcagatac caaatactgt ccttctagtg tagccgtagt taggccacca    3420
cttcaagaac tctgtagcac cgcctacata cctcgctctg ctaatcctgt taccagtggc    3480
tgctgccagt ggcgataagt cgtgtcttac cgggttggac tcaagacgat agttaccgga    3540
taaggcgcag cggtcgggct gaacggggg ttcgtgcaca cagcccagct tggagcgaac    3600
gacctacacc gaactgagat acctacagcg tgagctatga gaaagcgcca cgcttcccga    3660
agggagaaag gcggacaggt atccggtaag cggcagggtc ggaacaggag agcgcacgag    3720
ggagcttcca gggggaaacg cctggtatct ttatagtcct gtcgggtttc gccacctctg    3780
acttgagcgt cgatttttgt gatgctcgtc aggggggcgg agcctatgga aaaacgccag    3840
caacgcggcc tttttacggt tcctggcctt ttgctggcct tttgctcaca tgttctttcc    3900
tgcgttatcc cctgattctg tggataaccg tattaccgcc tttgagtgag ctgataccgc    3960
tcgccgcagc cgaacgaccg agcgcagcga gtcagtgagc gaggaagcgg aagagcgcct    4020
gatgcggtat tttctcctta cgcatctgtg cggtatttca caccgcatat ggtgcactct    4080
cagtacaatc tgctctgatg ccgcatagtt aagccagtat acactccgct atcgctacgt    4140
gactgggtca tggctgcgcc ccgacacccg ccaacacccg ctgacgcgcc ctgacgggct    4200
tgtctgctcc cggcatccgc ttacagacaa gctgtgaccg tctccgggag ctgcatgtgt    4260
cagaggtttt caccgtcatc accgaaacgc gcgaggcagc agatcaattc gcgcgcgaag    4320
gcgaagcggc atgcataatg tgcctgtcaa atggacgaag cagggattct gcaaaccta    4380 tgctactccg tcaagccgtc aattgtctga ttcgttacca attatgacaa cttgacggct    4440
acatcattca cttttcttc acaaccggca cggaactcgc tcgggctggc cccggtgcat    4500
tttttaaata cccgcgagaa atagagttga tcgtcaaaac caacattgcg accgacggtg    4560
gcgataggca tccgggtggt gctcaaaagc agcttcgcct ggctgatacg ttggtcctcg    4620
cgccagctta agacgctaat ccctaactgc tggcggaaaa gatgtgacag acgcgacggc    4680
gacaagcaaa catgctgtgc gacgctggcg atatcaaaat tgctgtctgc caggtgatcg    4740
ctgatgtact gacaagcctc gcgtacccga ttatccatcg gtggatggag cgactcgtta    4800
atcgcttcca tgcgccgcag taacaattgc tcaagcagat ttatcgccag cagctccgaa    4860
tagcgccctt cccctttgccc ggcgttaatg atttgcccaa acaggtcgct gaaatgcggc    4920
tggtgcgctt catccgggcg aaagaacccc gtattggcaa atattgacgg ccagttaagc    4980
cattcatgcc gtaggcgcg cggacgaaag taaacccact ggtgatacca ttcgcgagcc    5040
tccggatgac gaccgtagtg atgaatctct cctggcggga acagcaaaat atcacccggt    5100
```

-continued

```
cggcaaacaa attctcgtcc ctgattttc accaccccct gaccgcgaat ggtgagattg      5160
agaatataac ctttcattcc cagcggtcgg tcgataaaaa aatcgagata accgttggcc      5220
tcaatcggcg ttaaaccgc caccagatgg gcattaaacg agtatcccgg cagcagggga      5280
tcattttgcg cttcagccat acttttcata ctcccgccat tcagag                    5326
```

<210> SEQ ID NO 7
<211> LENGTH: 423
<212> TYPE: PRT
<213> ORGANISM: Homo sapiens

<400> SEQUENCE: 7

```
Met Lys Lys Leu Leu Phe Ala Ile Pro Leu Val Val Pro Phe Tyr Ser
1               5                   10                  15

His Ser Thr Met Glu Leu Glu Glu Pro Ala Val Tyr Phe Lys Glu Gln
            20                  25                  30

Phe Leu Asp Gly Asp Gly Trp Thr Ser Arg Trp Ile Glu Ser Lys His
        35                  40                  45

Lys Ser Asp Phe Gly Lys Phe Val Leu Ser Ser Gly Lys Phe Tyr Gly
    50                  55                  60

Asp Glu Glu Lys Asp Lys Gly Leu Gln Thr Ser Gln Asp Ala Arg Phe
65                  70                  75                  80

Tyr Ala Leu Ser Ala Ser Phe Glu Pro Phe Ser Asn Lys Gly Gln Thr
                85                  90                  95

Leu Val Val Gln Phe Thr Val Lys His Glu Gln Asn Ile Asp Cys Gly
            100                 105                 110

Gly Gly Tyr Val Lys Leu Phe Pro Asn Ser Leu Asp Gln Thr Asp Met
        115                 120                 125

His Gly Asp Ser Glu Tyr Asn Ile Met Phe Gly Pro Asp Ile Cys Gly
    130                 135                 140

Pro Gly Thr Lys Lys Val His Val Ile Phe Asn Tyr Lys Gly Lys Asn
145                 150                 155                 160

Val Leu Ile Asn Lys Asp Ile Arg Cys Lys Asp Asp Glu Phe Thr His
                165                 170                 175

Leu Tyr Thr Leu Ile Val Arg Pro Asp Asn Thr Tyr Glu Val Lys Ile
            180                 185                 190

Asp Asn Ser Gln Val Glu Ser Gly Ser Leu Glu Asp Asp Trp Asp Phe
        195                 200                 205

Leu Pro Pro Lys Lys Ile Lys Asp Pro Asp Ala Ser Lys Pro Glu Asp
    210                 215                 220

Trp Asp Glu Arg Ala Lys Ile Asp Asp Pro Thr Asp Ser Lys Pro Glu
225                 230                 235                 240

Asp Trp Asp Lys Pro Glu His Ile Pro Asp Pro Asp Ala Lys Lys Pro
                245                 250                 255

Glu Asp Trp Asp Glu Glu Met Asp Gly Glu Trp Glu Pro Pro Val Ile
            260                 265                 270

Gln Asn Pro Glu Tyr Lys Gly Glu Trp Lys Pro Arg Gln Ile Asp Asn
        275                 280                 285

Pro Asp Tyr Lys Gly Thr Trp Ile His Pro Glu Ile Asp Asn Pro Glu
    290                 295                 300

Tyr Ser Pro Asp Pro Ser Ile Tyr Ala Tyr Asp Asn Phe Gly Val Leu
305                 310                 315                 320

Gly Leu Asp Leu Trp Gln Val Lys Ser Gly Thr Ile Phe Asp Asn Phe
                325                 330                 335
```

-continued

```
Leu Ile Thr Asn Asp Glu Ala Tyr Ala Glu Glu Phe Gly Asn Glu Thr
            340                 345                 350

Trp Gly Val Thr Lys Ala Ala Glu Lys Gln Met Lys Asp Lys Gln Asp
        355                 360                 365

Glu Glu Gln Arg Leu Lys Glu Glu Glu Asp Lys Lys Arg Lys Glu
    370                 375                 380

Glu Glu Ala Glu Asp Lys Glu Asp Asp Asp Lys Asp Glu Asp
385                 390                 395                 400

Glu Glu Asp Glu Asp Lys Glu Glu Asp Glu Glu Asp Val Pro
                405                 410                 415

Gly Gln Ala Lys Asp Glu Leu
            420

<210> SEQ ID NO 8
<211> LENGTH: 17
<212> TYPE: PRT
<213> ORGANISM: Homo sapiens

<400> SEQUENCE: 8

Met Leu Leu Ser Val Pro Leu Leu Leu Gly Leu Leu Gly Leu Ala Val
1               5                   10                  15

Ala

<210> SEQ ID NO 9
<211> LENGTH: 5
<212> TYPE: PRT
<213> ORGANISM: Homo sapiens

<400> SEQUENCE: 9

Glu Pro Ala Val Tyr
1               5

<210> SEQ ID NO 10
<211> LENGTH: 24
<212> TYPE: PRT
<213> ORGANISM: Homo sapiens

<400> SEQUENCE: 10

Met Lys Lys Leu Leu Phe Ala Ile Pro Pro Leu Val Val Pro Phe Tyr
1               5                   10                  15

Ser His Ser Thr Met Glu Leu Glu
            20

<210> SEQ ID NO 11
<211> LENGTH: 21
<212> TYPE: DNA
<213> ORGANISM: artificial sequence
<220> FEATURE:
<223> OTHER INFORMATION: primer

<400> SEQUENCE: 11
atgccatagc atttttatcc a                                          21

<210> SEQ ID NO 12
<211> LENGTH: 20
<212> TYPE: DNA
<213> ORGANISM: artificial sequence
<220> FEATURE:
<223> OTHER INFORMATION: primer

<400> SEQUENCE: 12
gagatggacg gagagtggga                                            20
```

```
<210> SEQ ID NO 13
<211> LENGTH: 20
<212> TYPE: DNA
<213> ORGANISM: artificial sequence
<220> FEATURE:
<223> OTHER INFORMATION: primer

<400> SEQUENCE: 13
acagattaaa tcagaacgca                                          20
```

COMPOSITIONS AND METHODS FOR PURIFYING CALRETICULIN

This application claims priority to U.S. provisional application No. 61/096,185, filed Sep. 11, 2008, the contents of which are hereby incorporated by reference in their entirety.

FIELD OF THE INVENTION

The present invention relates to compositions and methods for expressing non-tagged human calreticulin and methods for purification of the non-tagged protein.

BACKGROUND OF THE INVENTION

Purified proteins are produced in systems for a wide range of applications in biology and biotechnology. These include research into cellular and molecular function, production of proteins as biopharmaceuticals or diagnostic reagents, and modification of the traits or phenotypes of livestock and crops.

Affinity protein tags are used as tools for purifying proteins from crude extracts. Protein tags are peptide sequences genetically grafted onto a recombinant protein. Often these tags are removable by chemical agents or by enzymatic means, such as proteolysis or intein splicing. Tags are attached to proteins for various purposes. Elutable affinity tags to purify proteins can be utilized in diverse cell systems including in *Escherichia coli*, yeast, *Drosophila*, and HeLa extracts.

Affinity tags are appended to proteins so that they can be purified from their crude biological source using an affinity technique. These include chitin binding protein (CBP), maltose binding protein (MBP), and glutathione-s-transferase (GST). The poly(His) tag is the most widely-used protein tag and it binds to metal matrices.

Solubilization tags are used, especially for recombinant proteins expressed in chaperone-deficient species such as *E. coli*, to assist in the proper folding in proteins and keep them from precipitating. These include thioredoxin (TRX) and poly(NANP). Some affinity tags have a dual role as a solubilization agent, such as MBP, and GST.

Chromatography tags are used to alter chromatographic properties of the protein to afford different resolution across a particular separation technique. Often, these consist of polyanionic amino acids, such as FLAG tag.

Epitope tags are short peptide sequences which are chosen because high-affinity antibodies can be reliably produced in many different species. These are usually derived from viral genes, which explain their high immunoreactivity. Epitope tags include V5-tag, c-myc-tag, and HA-tag. These tags are particularly useful for western blotting and immunoprecipitation experiments, although they also find use in antibody purification.

Fluorescence tags are used to give visual readout on a protein. GFP and its variants are the most commonly used fluorescence tags. More advanced applications of GFP include using it as a folding reporter (fluorescent if folded, colorless if not).

Protein tags find many other usages, such as specific enzymatic modification (such as biotin ligase tags) and chemical modification (FLaSH) tag. Often tags are combined to produce multifunctional modifications of the protein. However, with the addition of each tag comes the risk that the native function of the protein may be abolished or compromised by interactions with the tag.

For pharmaceutical production, tagged proteins are undesirable and require an extra step of removal of the tags after the purification step. The expression and production of the protein product with the tag can cause conformation changes in the protein resulting in diminished activity, even after the removal of the tag. Additionally, it is difficult to completely remove the tagged protein, leading to the presence of residual impurities in the protein sample. Thus, there is a need for expression and purification systems for producing heterologous proteins without relying on affinity tags for purification. Additionally, there is a need for economical and efficient methods for producing heterologous proteins in bacterial systems.

SUMMARY OF THE INVENTION

The present invention relates to compositions and methods for expressing human calreticulin and methods for purification of the protein product that is free of an affinity tag or label.

In certain embodiments, the invention encompasses a method for producing calreticulin comprising: (a) culturing a microorganism having a calreticulin gene under suitable culture conditions; (b) inducing expression of the calreticulin gene to produce a calreticulin protein product that is free of an affinity label or tag; and (c) purifying the calreticulin product. In certain embodiments, the microorganism is bacteria. In yet additional embodiments, the bacteria is *Escherichia coli*.

In certain embodiments, the calreticulin gene is human calreticulin. In yet additional embodiments, the calreticulin gene comprises SEQ ID NO:3.

In certain embodiments, the purifying comprises at least one ion chromatography purification followed by at least one hydrophobic chromatography purification. In certain embodiments, the purifying comprises two sequential ion chromatography purifications followed by at least one hydrophobic chromatography purification. In certain embodiments, the hydrophobic chromatography step comprises utilizing 20-25% ammonium sulfate for elution.

In yet additional embodiments, the invention relates to a method for expressing calreticulin in a prokaryotic cell, which comprises:

a) culturing a prokaryotic cell comprising a vector under conditions conducive to gene expression, wherein the vector comprises a nucleic acid encoding calreticulin, an origin of replication, and at least one selectable marker, and wherein the nucleic acid is operatively associated with an expression control sequence;

b) inducing expression of the calreticulin gene to produce a calreticulin protein product that is free of an affinity label or tag; and c) purifying said calreticulin protein product.

In certain embodiments, the prokaryotic cell is *E. coli*. In certain embodiments, the selectable marker is Kanamycin or Ampicillin. In yet additional embodiments, the purifying comprises at least one ion chromatography purification followed by at least one hydrophobic chromatography purification. In certain embodiments, the purifying comprises two sequential ion chromatography purifications followed by at least one hydrophobic chromatography purification. In certain embodiments, the hydrophobic chromatography step comprises utilizing 20-25% ammonium sulfate for elution.

In yet further embodiments, the invention encompasses a vector comprising an origin of replication, at least one selectable marker, and a multiple cloning site comprising a nucleic acid encoding calreticulin, and wherein the nucleic acid is operatively associated with an expression control sequence.

In certain embodiments, the calreticulin is human calreticulin. In additional embodiments, the calreticulin gene comprises SEQ ID NO:3. In certain embodiments, the selectable marker is Kanamycin or Ampicillin. In certain embodiments, the vector comprises the vector map of FIG. 5. In yet additional embodiments, the origin of replication is an *E. coli* origin.

In yet further embodiments, the invention relates to a host cell transformed with any of the vectors described herein.

In yet additional embodiments, the invention encompasses isolated and purified calreticulin, prepared by any one of the methods described herein.

BRIEF DESCRIPTION OF DRAWINGS

FIGS. 6A-D is the nucleotide sequence of the pBAD-hCRT vector (SEQ ID NO:6) including human calreticulin along with its amino acid sequence (SEQ ID NO:7) including the unique signal sequence from the pBAD construct. The boxed sequences correspond to the primers used for PCR or sequence analysis (SEQ ID NO:11 is GL96-seq.F; SEQ ID NO:12 is YQ15-seq.R; and SEQ ID NO:13 is G197-SEQ.R).

DESCRIPTION OF THE INVENTION

Figure 1:
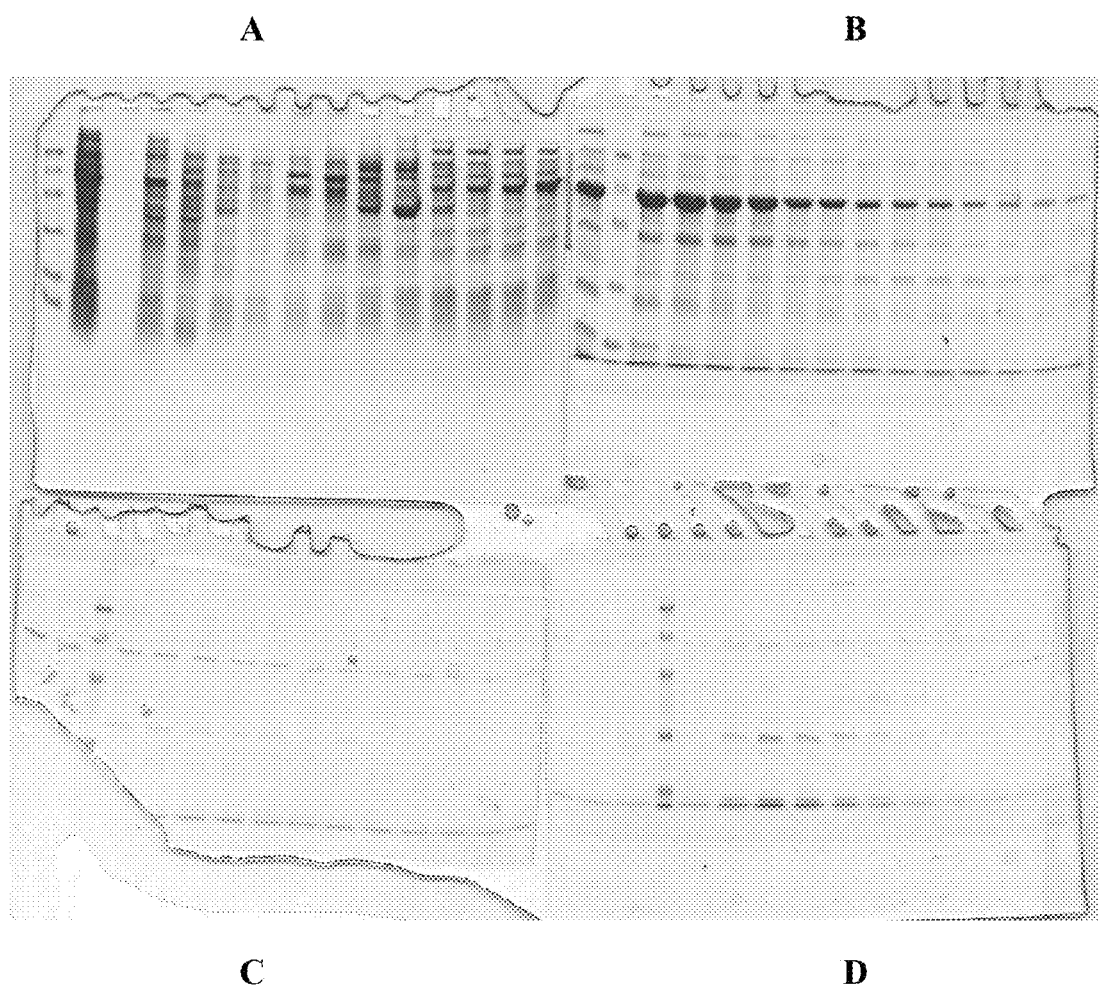
FIGS. 1A-D are photos of Coomassie Blue gels with protein samples from Q Sepharose fractions.
Figure 2:
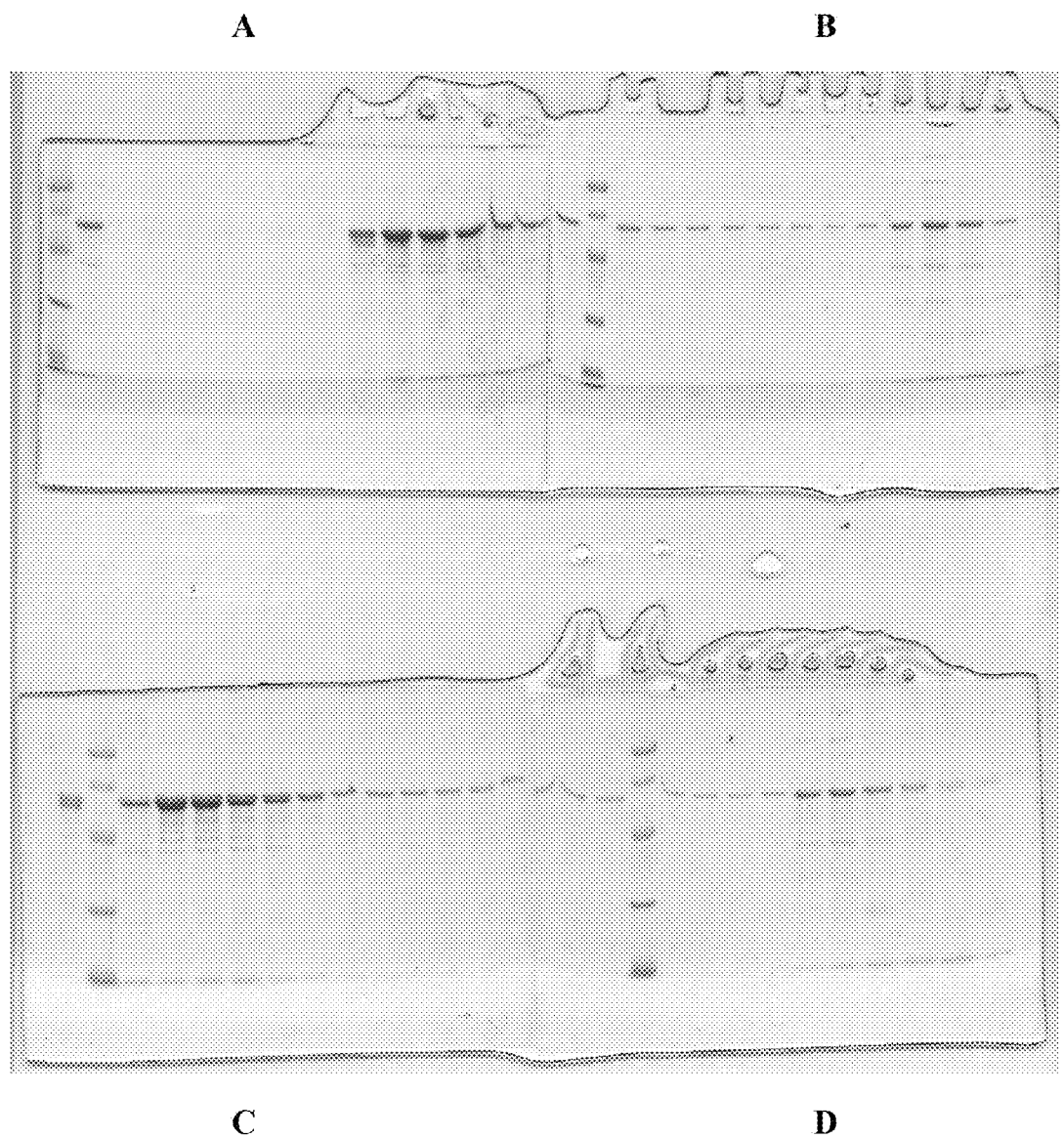
FIGS. 2A-D are photos of SDS-PAGE gels with HTP purified human calreticulin fractions.
Figure 3:
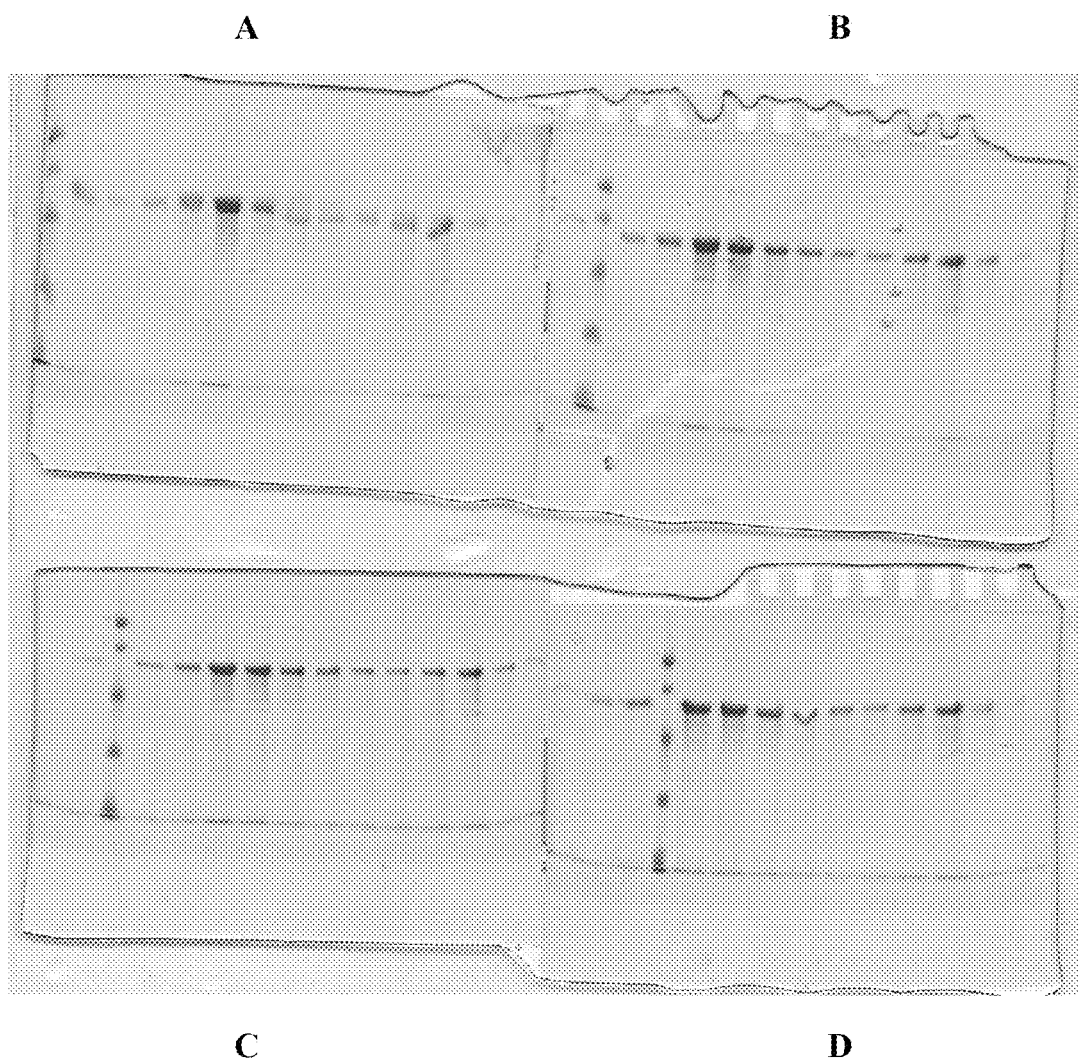
FIGS. 3A-D are photos of SDS-PAGE gels of Resource ISO purified human calreticulin fractions.

The present invention relates generally to purified proteins and methods for expressing a heterologous protein in a bacterial expression system without utilizing an affinity tag or label. In particular, the present invention provides a method for producing large quantities of calreticulin that is free of an affinity tag. The present invention also includes various aspects of biological materials and intermediates useful in the production of such non-tagged calreticulin by biological production.

The invention encompasses a method for producing calreticulin comprising: (a) culturing a microorganism having a calreticulin gene under suitable culture conditions; (b) inducing expression of the calreticulin gene to produce a calreticulin protein product that is free of an affinity label or tag; and (c) purifying the calreticulin product. In particular embodiments, the method utilizes a cDNA construct for calreticulin that terminates with a stop codon, such that the sequences encoding the expression tag(s) (i.e., c-myc and HIS-tag) from the expression vector are not translated and are not incorporated into the expressed protein.

Additionally, in a further embodiment, the present methods utilize a combination of at least two sequential ion chromatography purification steps followed by one hydrophobic chromatography purification step. In certain preferred embodiments, the hydrophobic chromatography step comprises utilizing 20-25% ammonium sulfate for elution. The ammonium sulfate elution step resulted in an excellent purification profile and was surprising in view of the failure of such a step to work in many other hydrophobic chromatography methods.

Even though high amounts of tagged calreticulin can be obtained using standard expression techniques, attempts to remove the tag generate impurities and may cause problems for its use in pharmaceutical/clinical applications.

The purification of calreticulin using the presently described expression system and three-step chromatography purification procedure provides a process for manufacturing significant quantities (suitable for large scale manufacture of a commercial pharmaceutical product) of purified human calreticulin lacking an affinity tag or label that is suitable for pharmaceutical use and analysis.

Calreticulin (CRT), also known as calregulin, is a well conserved chaperone protein that is found in most cells and has a variety of functions. It binds calcium with high capacity and interacts with newly synthesized proteins in the ER to facilitate their folding and to prevent aggregation. It is also expressed in cytotoxic granules where it is believed to regulate the activity of the cytolytic molecule, perforin. The cDNA sequence encoding the of human calreticulin precursor has been determined and has GenBank Accession No. NM_004343 (SEQ ID NO:3, 1899 bp). The amino acid sequence of the human calreticulin precursor protein has also been described at GenBank Accession No. NP_004334 (SEQ ID NO:4, 417 amino acids). Other names for calreticulin include: CRT, SSA, cC1qR, FLJ26680.

It is noted that the human calreticulin signal sequence MLLSVPLLLGLLGLAVA (SEQ ID NO:8) from the precursor protein is cleaved to produce the mature protein starting with the residues EPAVY . . . (SEQ ID NO:9). The unique signal sequence MKKLLFAIPPLVVPFYSHSTMELE (SEQ ID NO:10) preceding the mature calreticulin sequence is co-translationally cleaved to produce a secreted mature protein in the pBAD construct.

Calreticulin was first identified in skeletal muscle sarcoplasmic reticulum. Recently, it has been shown that calreticulin modulates the expression of hormonally regulated genes and has also been localized in other cellular organelles, supporting the idea that it functions outside the endoplasmic reticulum. Calreticulin is a multifunctional protein that acts as a major $Ca^{2+}$-binding (storage) protein in the lumen of the endoplasmic reticulum. It is also found in the nucleus, suggesting that it may have a role in transcription regulation. Calreticulin binds to the synthetic peptide KLGFFKR (SEQ ID NO:5), which is almost identical to an amino acid sequence in the DNA-binding domain of the superfamily of nuclear receptors. Calreticulin binds to antibodies in certain sera of systemic lupus and Sjogren patients which contain anti-Ro/SSA antibodies, it is highly conserved among species, and it is located in the endoplasmic and sarcoplasmic reticulum where it may bind calcium. The amino terminus of calreticulin interacts with the DNA-binding domain of the glucocorticoid receptor and prevents the receptor from binding to its specific glucocorticoid response element. Calreticulin can inhibit the binding of androgen receptor to its hormone-responsive DNA element and can inhibit androgen receptor and retinoic acid receptor transcriptional activities in vivo, as well as retinoic acid-induced neuronal differentiation. Thus, calreticulin can act as an important modulator of the regulation of gene transcription by nuclear hormone receptors. Increased autoantibody titer against human calreticulin is found in infants with complete congenital heart block of both the IgG and IgM classes.

Three putative structural domains were identified in calreticulin: a globular N-terminal domain, a praline-rich P domain, and an acidic C-terminal tail domain. High- and low-affinity binding of $Ca^{2+}$ to calreticulin is restricted to the P and C domains, respectively. The globular N-terminal domain was shown to have affinity for the cytoplasmic domain of the alpha subunit of integrins and for a family of steroid receptors.

Suitable biological systems for producing calreticulin include prokaryotic systems.

The preferred prokaryote is *Escherichia coli* (*E. coli*). *E. coli* is well established as an industrial microorganism used in the production of metabolites (amino acids, vitamins) and several recombinant proteins. The entire *E. coli* genome has also been sequenced, and the genetic systems are highly developed. [Fujisaki, et. al, J. Biochem. 108, 995-1000 (1990); Lois et al., Proc. Natl. Acad. Sci. USA, 95, 2105-2110 (1998); Hemmi et al., J. Biochem., 123, 1088-1096 (1998)].

Suitable organisms useful in producing calreticulin are available from numerous sources, such as the American Type Culture Collection (ATCC), Rockville, Md., Culture Collection of Algae (UTEX), Austin, Tex., the Northern Regional Research Laboratory (NRRL), Peoria, Ill. and the *E. coli* Genetic Stock Center (CGSC), New Haven, Conn. The present invention is not limited by the host cells employed.

Such expression organisms i.e., engineered host cells, can be cultured in conventional nutrient media modified as appropriate for activating promoters, selecting transformants, or amplifying the calreticulin gene. Culture conditions, such as temperature, pH and the like, are those previously used with the host cell selected for expression, and will be apparent to those skilled in the art and in the references cited herein, including, e.g., Sambrook, Ausubel and Berger, as well as e.g., Freshney (1994) Culture of Animal Cells: A Manual of Basic Technique, 3.sup.rd ed. (Wiley-Liss, New York) and the references cited therein.

In certain aspects of the invention, the cells used in the cell culture are genetically modified to increase the yield of calreticulin. Cells may be genetically modified by genetic engineering techniques (i.e., recombinant technology), classical microbiological techniques, or a combination of such techniques and can also include naturally occurring genetic variants. Some of such techniques are generally disclosed, for example, in Sambrook et al., 1989, Molecular Cloning: A Laboratory Manual, Cold Spring Harbor Labs Press. The reference Sambrook et al., ibid., is incorporated by reference herein in its entirety. A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect of increased yields of calreticulin within the microorganism or in the culture supernatant.

As used herein, genetic modifications which result in a decrease in gene expression, in the function of the gene, or in the function of the gene product (i.e., the protein encoded by the gene) can be referred to as inactivation (complete or partial), deletion, interruption, blockage or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity). Genetic modifications which result in an increase in gene expression or function can be referred to as amplification, overproduction, overexpression, activation, enhancement, addition, or up-regulation of a gene. Addition of cloned genes to increase gene expression can include maintaining the cloned gene(s) on replicating plasmids or integrating the cloned gene(s) into the genome of the production organism. Furthermore, increasing the expression of desired cloned genes can include operatively linking the cloned gene(s) to native or heterologous transcriptional control elements.

In certain embodiments, expression of calreticulin is induced in bacterial transformants with isopropylthiogalactoside (IPTG). In certain embodiments, the transformation mix is plated on agar plates made in L-Broth containing 100 μg/ml ampicillin.

Calreticulin has been shown to be useful in promoting the scarless healing of wounds in humans (See U.S. Pat. No. 5,591,716) and is therefore a desirable pharmaceutical agent for this purpose. Calreticulin may also have other useful pharmaceutical applications. Thus, a procedure for producing large quantities of pure (tag-free) calreticulin (for use in a commercial/pharmaceutical product) would be of value. Calreticulin produced according to the methods described herein can be scaled up for production in fermenters by growing the expression strain containing for example, the pBAD/gIII A –hCRT vector under suitable conditions for inducing expression of calreticulin.

Molecular Biology

Conventional molecular biology, microbiology, and recombinant DNA techniques within the skill of the art may be employed, in accordance with this invention. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994).

The term "selection marker or selectable marker" is typically used to refer to a gene and/or protein whose presence can be detected directly or indirectly in a cell, for example, a gene and/or a protein that inactivates a selection agent and protects the host cell from the agent's lethal or growth-inhibitory effects (e.g., an antibiotic resistance gene and/or protein). Another possibility is that the selection marker induces fluorescence or a color deposit (e.g., green fluorescent protein and derivatives, luciferase, or alkaline phosphatase).

The term "selection agent" is typically defined as a chemical compound that is able to kill or retard the growth of host cells (e.g., an antibiotic).

The term "selection" is typically defined as the process of using a selection marker/selectable marker and a selection agent to identify host cells with specific genetic properties (e.g., that the host cell contains a transgene integrated into its genome).

"Amplification" of DNA as used herein denotes the use of polymerase chain reaction (PCR) or other methods to increase the concentration of a particular DNA sequence within a mixture of DNA sequences. For a description of PCR see Saiki et al., Science 1988, 239:487.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "polynucleotide" or "nucleotide sequence" is a series of nucleotide bases (also called "nucleotides" in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "promoter" or "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. The promoter may be operatively associated with other expression control sequences, including enhancer and repressor sequences.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene", means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A coding sequence is "under the control of" or "operatively associated with" expression control sequences in a cell when RNA polymerase transcribes the coding sequence into RNA, particularly mRNA, which is then trans-RNA spliced (if it contains introns) and translated into the protein encoded by the coding sequence.

The term "expression control sequence" refers to a promoter and any enhancer or suppression elements that combine to regulate the transcription of a coding sequence. In a preferred embodiment, the element is an origin of replication.

The terms "vector", "cloning vector", and "expression vector" mean the vehicle by which a DNA or RNA sequence (e.g. a foreign gene) can be introduced into a host cell, so as to transform the host and promote expression (e.g. transcription and translation) of the introduced sequence.

Vectors typically comprise the DNA of a transmissible agent, into which foreign DNA is inserted. A common way to insert one segment of DNA into another segment of DNA involves the use of specific enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct". A common type of vector is a "plasmid" which generally is a self-contained molecule of double-stranded DNA, usually of bacterial origin, that can readily accept additional (foreign) DNA and which can be readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence that initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes. Vector constructs may be produced using conventional molecular biology and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); F. M. Ausubel et al. (eds.), Current Protocols in Molecular Biology, John Wiley & Sons, Inc. (1994).

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign (i.e., extrinsic or extracellular) gene or foreign nucleic acid into a cell. The term "transformation" means the introduction of a foreign gene, foreign nucleic acid, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme.

The term "expression system" means a host cell and compatible vector under suitable conditions, e.g. for the expression of a protein coded for by foreign DNA carried by the vector and introduced to the host cell. In a specific embodiment, the host cell of the present invention is a Gram-negative or Gram-positive bacteria. These bacteria include, but are not limited to, *Escherichia coli* (*E. coli*).

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed.

The terms "mutant" and "mutation" mean any detectable change in genetic material, e.g. DNA, or any process, mechanism, or result of such a change. This includes gene mutations, in which the structure (e.g., DNA sequence) of a gene is altered, any gene or DNA arising from any mutation process, and any expression product (e.g., protein or enzyme) expressed by a modified gene or DNA sequence. The term "variant" may also be used to indicate a modified or altered gene, DNA sequence, enzyme, cell, etc., i.e., any kind of mutant.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, more preferably at least 85%, most preferably at least 90%, and which has the same or substantially similar properties or functions as the native or parent protein or enzyme to which it is compared.

As used herein, the terms "homologous" and "homology" refer to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs at conserved positions.

Accordingly, the term "sequence similarity" refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90 or 95% of the nucleotides match over the defined length of the DNA sequences, as determined by sequence comparison algorithms, such as BLAST, FASTA, DNA Strider, etc. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar. Preferably, the amino acids are functionally identical. Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 5×Denhardt's, and no formamide; or 30% formamide, 5×SSC, 0.5% SDS, 5×Denhardt's). Moderate stringency hybridization conditions correspond to a higher $T_m$, e.g., 40% formamide, with 5× or 6×SCC, 5×Denhardt's. High stringency hybridization conditions correspond to the highest $T_m$, e.g., 50% formamide, 5× or 6×SCC, 5×Denhardt's. SCC is a 0.15M NaCl, 0.015M Na-citrate buffer. 5×Denhardt's is 0.1% ficoll, 0.1% g polyvinylpyrrolidone (MW40,000), 0.1% g BSA (w/v). Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids encoding the protein. In a further embodiment, an oligonucleotide of the invention can form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "prokaryotic cell" or "prokaryote" refers to a cell without discrete nucleus and with single, circular DNA molecules within the cytoplasm. Prokaryotes include but are not limited to cells of bacteria and blue green algae.

Abbreviations are as follows: HPLC refers to high-performance liquid chromatography; GC and % GC refer to the number and percentage of guanine and cytosine bases; CFU refers to colony forming units.

EXAMPLES

The present invention will be better understood by reference to the following Examples, which are provided as exemplary of the invention, and not by way of limitation.

General Materials and Methods

DNA restriction and modification enzymes and T4 DNA ligase were obtained from New England Biolabs. Plasmid DNA was isolated using commercial kits and DNA fragments were purified using commercial kits (Qiagen, Valencia, Calif.). Competent E. coli cells (i.e., DH5α, BL21 cells) were obtained from Novagen (Merck/EMD, San Diego, Calif.). TOP10F' Rosetta cells for expression studies for human calreticulin were obtained from Invitrogen (Carlsbad, Calif.). Standard cloning and molecular biology kits and related techniques were used according to manufacturer's specifications and with buffers and reagents supplied by the manufacturer. Antibiotics were purchased from Sigma.

Example 1

Cloning of the Human Calreticulin cDNA

PCR reactions were carried out under standard, manufacturers conditions unless otherwise noted. Likewise, except where noted, standard molecular techniques such as restriction endonuclease digestions and ligations may be carried out under any suitable standard conditions.

The PCR-driven amplification of human calreticulin cDNA (ATCC clone #3767728, GenBank accession #AW239363) was carried out using the following sets of primers:

```
                                                   (SEQ ID NO: 1)
Forward: 5'-ATA CTC GAG GAG CCT GCC GTC TAC-3'

(SEQ ID NO: 2)
Reverse: 5'-AGG GAA TTC CTA CAG CTC GTC C-3'
```

The underlined EcoR1 and restriction sites were used for cloning. In certain experiments, the primers (SEQ ID NO:11) GL96-seq.F: ATGCCATAGCATTTTTATCCA and (SEQ ID NO:13) G197-SEQ.R: ACAGATTAAATCAGAACGCA were used.

Human calreticulin was amplified according to the following procedure:

1. Human calreticulin cDNA was amplified from plasmid pPIC9-human CRT (ATCC Accession No.: AW239363) using the following PCR reaction conditions:

| | |
|---|---|
| 10 x buffer | 5 µl |
| 10 mM dNTP: | 1.5 µl |
| 50 mM MgSO$_4$: | 1 µl |
| 10 µM primer1 (SEQ ID NO: 1 or 11): | 1.5 µl |
| 10 µM primer2 (SEQ ID NO: 2 or 13): | 1.5 µl |
| Template DNA: | 2 µl (100 ng) |
| Pfx (Invitrogen): | 0.5 µl |
| H$_2$O: | to final volume 50 µl |

| PCR cycles: | 94° C. | 3 min | |
| | 94° C. | 30 s | |
| | 58° C. | 30 s | } 30 cycles |
| | 68° C. | 1 min 30 s | |
| | 72° C. | 3 min, then keep in 4° C. | |

2. Run 1% agarose gel to confirm PCR product (expected size of 1899 nucleotides, about a 1900 base pair band on gel).

The calreticulin PCR product was confirmed by sequencing and then digested and ligated to a suitable vector according to the following procedures:

3. The hCRT PCR product was digested with Xho I and EcoR I under the following conditions:

| | |
|---|---|
| 10 x EcoR I buffer: | 5 µl |
| Xho I: | 1 µl |
| EcoR I: | 1 µl |
| PCR product: | 45 µl |

Incubated at 37° C. overnight.

The pBAD gIII A vector was prepared by digesting vector DNA with Xho I and EcoR I under the following conditions:

| | |
|---|---|
| 10 x EcoR I buffer: | 5 µl |
| Xho I: | 1 µl |
| EcoR I: | 1 µl |
| pBAD vector DNA: | 500 ng |
| H$_2$O: | to final volume 50 µl |

Incubated at 37° C. overnight.

4. The digested PCR product and vector were purified using a gel purification kit according to the manufacturer's instructions (Qiagen).
5. A 1% agarose gel was run to examine the concentration of PCR product and vector.
6. The purified PCR product and vector were ligated under the following conditions:

| | |
|---|---|
| 10 x ligation buffer: | 2 µl |
| Purified PCR product: | 100 ng |
| Purified pBAD vector: | 50 ng |
| T4 ligase: | 1 µl |
| H$_2$O: | to final volume 50 µl |

The ligation reaction was incubated at room temperature for 4 hours.

7. Competent *E. coli* cells were transformed as follows:
   Add 5 µl ligation product into 50 µl DH5α competent *E. coli* cells;
   Incubate mixture on ice for 30 min;
   Heat shock at 42° C. for 90 seconds;
   Incubate on ice for 2 min;
   Add product to glass tube with 250 µl LB and grow for 1 hour in 37° C. shaker;
   Plate total content to LB-Amp plates;
   Grow plates overnight at 37° C.

8. Picked colonies and screened for positive clones using antibiotic resistance, restriction digestion, and nucleotide sequence analysis. The nucleotide sequence analysis, based on reference SEQ ID NO:3 was also carried out on the positive clones to verify the calreticulin insert (various primers were used for sequencing including: SEQ ID NO:11 (GL96-seq.F): ATGCCATAGCATTTTTATCCA; SEQ ID NO:12; YQ15-seq.R (1101): GAGATGGACG-GAGAGTGGGA; and SEQ ID NO:13 (G197-SEQ.R): ACAGATTAAATCAGAACGCA. The DH5α construct was used as the stock strain. The pBAD/gIII-A hCRT vector was transformed into BL21 expression cells from Novagen (Merck/EMD, San Diego, Calif.) for expression of human calreticulin, as described below.

Example 2

Expressing and Purifying Human Calreticulin in *E. coli* pBAD expression vectors encoding human calreticulin (pBADhCRT) were made as described in Example 1. While both amp and kan resistant vectors are available, the Kan resistant clone has slightly increased level of expression and is preferred by the FDA for pharmaceutical purposes. While numerous suitable expression strains can be used, the *E. coli* strain used for expression in the present examples, was Rosetta (obtained from Invitrogen (Carlsbad, Calif.) TOP10F'. Prior to protein purification, the pH of each buffer was confirmed. For protein purification, all work was performed in the cold room unless specified. Protease inhibitor cocktail+PMSF (phenylmethanesulphonylfluoride)+Benzamidine (for details see buffers composition section below)

were added to all buffers prior to use. The protease inhibitors are optional and may be omitted for the last chromatography step.

Buffers and Solutions for Protein Expression and Purification.

Lysate Buffer (L-Buffer)
150 mM NaCl
100 mM $KH_2PO_4$, pH-7.1
2 mM $MgCl_2$

Q Sepharose Chromatography Column Buffers
Column details: HiLoad 26/10 Fast Flow column was used from GE Healthcare Bio-Sciences cat #17-1062-01
Q Sepharose Binding buffer (BBQ)
150 mM NaCl
100 mM $KH_2PO_4$, pH-7.1
2 mM $MgCl_2$
Q Sepharose Elution buffer (EBQ)
1000 mM NaCl
100 mM $KH_2PO_4$, pH-7.1
2 mM $MgCl_2$ Hydroxylapatite Chromatography Column Buffers
Column details: Hydroxylapatite Bio-gel HTP Gel, Bio-Rad cat#130-0420
Binding buffer (BBH)
10 mM $K_2HPO_4$, pH-7.0
Wash buffer (WBH) (use 2 column volumes for washing)
80 mM $K_2HPO_4$, pH-7.0
Elution buffer (EBH) (for continuous salt gradient from 80-1000 mM)
80 mM $K_2HPO_4$, pH-7.0
1000 mM $K_2HPO_4$, pH-7.0

Resource Iso (Isopropyl) Chromatography Column Buffers
Column details: RESOURCE ISO 1 ml column from GE Healthcare Bio-Sciences cat #17-1185-01
Binding buffer (BBI) Buffers:
40% Ammonium Sulfate in 10 mM $K_2HPO_4$, pH-7.2
Elution buffer (EBI)
10 mM $K_2HPO_4$, pH-7.2
Protein storage Buffer
10 mM Tris-HCl, pH-7.0
1 mM EDTA The protein may also be stored in calcium containing buffers as long as calcium concentration does not exceed 10 mM.

Protease Inhibitor Solutions
Protease Inhibitor Cocktail (2000× Stock):
The following recipe is for a 100 ml stock solution in 100% EtOH. Store at −20° C. as 2 ml aliquots.

| Aprotinin, Sigma Cat # A-1153 | 10 mg |
| Phosphoramidone, Sigma Cat # R-9382 | 5 mg |
| TLCK, Sigma Cat # T-7254 | 10 mg |
| TPCK, Sigma Cat # T-4376 | 20 mg |
| APMSF, Sigma Cat # A-6664 | 10 mg |
| E-64, Sigma Cat # E-3132 | 10 mg |
| Leupeptin, Sigma Cat # L-2884 | 5 mg |
| I Pepstatin, Sigma Cat # P-4265 | 2 mg |

50 μl of the protease inhibitor cocktail/100 ml of buffer was used in the experiments described herein.

PMSF Solution
Stock solution: 100 mM PMSF in 95% ETOH (Store chilled, i.e., in the refrigerator).
500 μl of PMSF stock solution/100 ml of buffer is used in the experiments described herein.

Benzamidine Solution
Stock solution: 200 mM Benzamidine in 95% ETOH. (Store chilled, i.e., in the refrigerator). 250 μl of benzamidine stock solution/100 ml of buffer was used in the experiments described herein.

*E. coli* Culture and Induction of Protein Expression
Chemicals/Solutions
Kanamycin (Kan) final concentration 30 μg/ml. Add 5 μl/ml (filter sterilized stock 60 mg/ml in dd$H_2O$, store at −20° C.).
Chloramphenicol (CM): final concentration 130 μg/ml. Add 30 μl/ml (filter sterilized stock 60 mg/ml, store at −20° C. in 95% ETOH).
Arabinose: final concentration 0.02% (filter sterilized stock 20% in dd$H_2O$, store at −20° C.). Use L-(+) Arabinose from Sigma, cat#A-3256 for the induction.

Calreticulin Expression in *E. coli*
Day 1. Streaked the LB/Kan/CM plate with *E. coli* harboring a pBAD-hCRT expression vector, incubated overnight (O/N—18-20 hrs) at 37° C.
Day 2. Inoculated 25 ml of LB/Kan/CM with single picked colony and incubated cells in a bacterial shaker overnight (O/N—18-20 hrs) at 37° C. and at 200 rpm.
Day 3. Added 10 ml of *E. coli* 0/N culture (point 2) at 1:50 dilution to 500 ml of LB/Kan/CM media in 2 L flask and incubated in a bacterial shaker at 37° C., at 200 rpm for approximately 3-4 hrs until the turbidity of the culture reaches $OD_{600}$. of 0.5-0.6.
Induction: Added 0.5 ml of 20% (stock) L-Arabinose and continued to incubate in a bacterial shaker at 30° C., 200 rpm for additional 4 hrs.

Centrifugation: Beckman centrifuge model #J2-21M using 250 ml centrifuge bottles; Rotor #JA-14, at 6,000 rpm (5,523×g) for 10 min at 4° C.

Re-suspended a pellet in 30 ml ice cold L-Buffer containing protease inhibitors.

French pressed the resuspended protein pellets twice at 1,000 psi, (French pressure Cell Press, American Instrument Company P1603013600), keep sample on ice. Retained 20 μl aliquot for SDS-PAGE analysis.

Centrifugation: Beckman centrifuge model #J2-21, 2×40 ml tubes, rotor JA-17, 10,000 rpm (13,776×g) for 20 min at 4° C.

Saved the supernatant (30 ml) containing calreticulin from the French press and kept at 4° C.

Added protease inhibitors to the calreticulin samples. Filtered the supernatant through a 0.22 μm filter using a syringe unit filter and proceeded to Q Sepharose chromatography step. Retained 20 μl aliquot for SDS-PAGE analysis.

Gently rinsed the pellet with a sterile dd$H_2O$ to remove any trace of supernatant and re-suspend in 5 ml of L-Buffer. Retain 20 μl aliquot for SDS-PAGE analysis.

Standard Laemmli gel electrophoresis was used to test for expression of calreticulin (e.g., SDS-PAGE, 10% acrylamide). Ten microliters of 3× Sample Buffer was added to 20 μl sample mix and loaded on SDS-PAGE in the following amounts:

| A-sample after French press | 15 μl |
| B-sample of the supernatant | 15 μl |
| C-sample of the pellet | 5 μl |

Purification Using Q Sepharose Column Chromatography

Before starting chromatography, the column was washed with 2-3 column volumes of binding buffer (BBQ). The following FPLC settings were used for Q Sepharose separation: Unicorn 5.11.

SDS-PAGE (10% acrylamide) was performed on every other fraction from the Q Sepharose column to identify the exact elution profile for calreticulin. Fractions containing human calreticulin were combined. FIGS. 1A-D are photos of SDS-PAGE gels showing the protein fractions from Q Sepharose chromatography. The Molecular Weight Standards (MWS or MW) used are Low range Bio-Rad cat#161-0304 as follows:
- →97,400 daltons Phosphorylase b
- →66,200 daltons Serum albumin
- →45,000 daltons Ovalbumin
- →31,000 daltons Carbonic anhydrose
- →21,500 daltons Trypsin inhibitor
- →14,400 daltons Lysozyme The samples in the gels shown in FIGS. 1A-D, a representative Q Sepharose chromatography purification using the an expression vector according to the present invention (pBAD-hCRT), are as follows:
Gel A (lanes from left to right)
L,B,FT,W1,W2,W3.W4, B12,B10,B10,B8,B6,B4,B2,C1, C3
Gel B (lanes from left to right)
C5,L,C7,C9,C11,D12,D10,D8,D6,D4,D2,E1,E3,E5,E7
Gel C (lanes from left to right)
E9,E11,L,F12,F10,F8,F6,F4,F2,G1,G3,G5,G7,G9,G11
Gel D (lanes from left to right)
H12,H8,H4,L,H2,I1,I3,I5,I6,I8,I8,I10,J12,J10,J8,J6
The sample abbreviations stand for:
L=Low molecular weight standards
B=sample before the column
FT=flow through
W=washes (1, 2, 3, 4)
B12-J6=fractions from Q Sepharose column
Each gel was loaded with 20 µl of each fraction/lane. Fractions C6 to E12 were pooled for further separation.

Pooled fractions C6 to E12 were dialyzed against 2 changes of 10 mM $K_2HPO_4$ pH-7.0 (for dialysis sample: buffer (v:v) ratio should be maintained at 1:1,000). A minimum of 6 hours was utilized for each buffer change. Dialysis can continue for longer, but does not have to exceed 8 hrs for each buffer change. Dialysis tubing used: Fisher Scientific Cat#21-152-14.

Samples were removed from dialysis tubing and filtered through a 0.22 µm syringe unit filter. The filtered samples were then subjected to hydroxylapatide chromatography. At this point, the sample should be clear, if not, centrifuge: Beckman centrifuge model #J2-21M; 40 ml centrifuge bottles; Rotor #JA-17, 10,000 rpm (13,776×g) for 10 min at 4° C. Discard pellet, collect supernatant and proceed to hydroxylapatite chromatography.

Hydroxylapatite (Htp) Column Chromatography

Preparation of Htp Beads and Column Chromatography

Using fresh beads each time for Htp chromatography is important for optimum results. Three columns of the same size were needed to process the Q Sepharose sample isolated as described above. The columns were prepared as follows:
1. 1.7 g of dry powder Bio-Gel HTP hydroxylapatite was weighed: column capacity 10 mg of protein/g. When hydrated, Bio-Gel HTP hydroxylapatite occupies approximately 2-3 ml per gram. 7 g of HPT in BBH buffer provided approximately 19-20 ml.
2. De-fining the beads. Added 1 part of HTP powder and 6 parts of binding buffer (BBH). Swirled gently, settled for 10 min and decanted the supernatant. Repeated this step 2 times.
3. Prepared slurry in binding buffer in a ratio of 75% settled gel to 25% buffer. Loaded the mixture onto a glass column: diameter: 20 mm; length: 13 cm.
4. Loaded ⅓ of Q Sepharose purified calreticulin onto each HTP column (divided equally among the 3 columns).

Before starting the program, wash the column with 2-3 column volumes of Binding buffer (BBH). The following FPLC settings were used for HTP column chromatography: Unicorn 5.11.

FIGS. 2A-D show SDS-PAGE gels of HTP purified human calreticulin. The Molecular Weight Standards were used— Low range Bio-Rad cat#161-0304:
- →97,400 daltons Phosphorylase b
- →66,200 daltons Serum albumin
- →45,000 daltons Ovalbumin
- →61,000 daltons Carbonic anhydrose
- →21,500 daltons Trypsin inhibitor
- →14,400 daltons Lysozyme The FIGS. 2A-D samples from an exemplary HTP chromatography (following the Q-Sepharose purification step) purification correspond from left to right to the following:
Gel #A
L,B,FT,W,A9,A10,A11,A12,B12,B11,B10,B9,B8,B7, B6,
Gel#B
B5,L,B4,B2,C1,C3,C5,C7,C10,D11,D9,D6,D4,D1,E5,
Fractions from B11 to C10 were pooled.
Gel #C
A11,A12,L,Before(B),B12,B11,B10,B9,B8,B7,B6,B5, b4,B3,B2,
Gel#D
B1,LC2,C4,L,C6,C8,C10,D12,D8,D6,D4,D2,E1,E7,
Fractions from A12 to C11 were pooled.
The sample abbreviations stand for:
L=molecular weight standards
B=sample before the column (Gel #A and #C)
FT=flow through
W=wash
Each gel was loaded with 20 µl of each fraction/lane.
FPLC—RESOURCE ISO (ISOPROPYL) CHROMATOGRAPHY The hydroxylapatite fractions containing calreticulin were combined and made saturated with solid ammonium sulfate to 40% (v/w). Two hundred forty-three grams of solid ammonium sulfate was then added to 1 L of solution. The solution was mixed gently and filter sterilized (Millipore 0.22 µm). The filtered sample was loaded into the Resource ISO column (hydrophobic chromatography step) with a flow rate of 1 ml/min. 1 ml resource ISO column, has a loading capacity of ~25 mg. Before starting the ISO chromatography step, the column was washed with 2-3 column volumes of Binding buffer (BBI). The ISO chromatography was performed as follows:
1. Column was stored in 20% ETOH.
2. Washed column first with $ddH_2O$, then equilibrate with a binding buffer
3. Washed with elution buffer.
4. Washed again with binding buffer.
5. Eluted the protein with a linear gradient of buffer BBI and buffer EBI, used 50 ml of each. Collected 0.5 ml fractions.
6. Analyzed every second fraction on SDS-PAGE (20 µl sample) (10% acrylamide).

Calreticulin eluted at approximately 20-25% ammonium sulfate.
The following FPLC setting was used for Resource ISO column chromatography: Unicorn 5.11.

FIGS. 3A-D show SDS-PAGE gels of Resource ISO purified calreticulin (i.e., calreticulin purified following the Q-Sepharose and HTP chromatography). The Molecular Weight Standards used are the Low range Bio-Rad cat#161-0304:
- →97,400 daltons Phosphorylase b
- →66,200 daltons Serum albumin
- →45,000 daltons Ovalbumin
- →431,000 daltons Carbonic anhydrose
- →21,500 daltons Trypsin inhibitor
- →14,400 daltons Lysozyme The samples from an exemplary Resource ISO chromatography correspond to the following lanes from left to right in FIGS. 3A-D:
Gel A run#1
L,B,A11,A12,B12,B11,B10,B9,B8,B7,B6,B5,B4,B3,B2,B1
Fractions from A12 to B6 were pooled.
Gel B run#2
C12,L,D12,D11,D10,D9,D8,D7,D6,D5,D4,D3,D2,D1,E1
Fractions from C12 to D5 were pooled.
Gel C run#3
E12,F12,LF1,F10,F9,F8,F7F6,F5,F4,F3,F2,F1,G1
Fractions from F12 to F4 were pooled.
Gel D run#4
H11,H10H9,L,H8,H7,H6H5,H4,H3,H2,H1,I1,I2,I3
Fractions from H11 to H4 were pooled.
The abbreviations are as follow:
L=molecular weight standards
B=sample before the column
FT=flow through
W=wash
The gels were loaded with 20 µl of each fraction/lane.

Filter Sterilization and Measurement of Protein Concentration

Following purification using any of the chromatography methods described herein, the protein samples can be filter sterilized using any suitable method.

1. In a preferred embodiment, the protein samples were filter sterilized using Millex Sterile Syringe Driven Filter Unit-0.22 µm from Millipore, cat#SLGV 033RS. This unit uses a 10 ml syringe, through which the calreticulin sample is pushed.
2. Next, the filter unit was rinsed by filtering protein storage buffer to recover any protein that may remain on the filter.
3. Any suitable means for concentrating the protein may be used. In a preferred embodiment, an Amicon Ultra15 Centrifuge Filter Unit from Millipore—cat #UFC9 03024, regenerated cellulose 30MWCO unit was utilized. The amicon was centrifuged at a maximum speed of 4,800 rpm (3,838×g) using, for example, a Beckman centrifuge GS-15R, swing bucket rotor #S4180.
4. Preferably, the protein is concentrated to a small volume (typically less than 1 ml). Next, the same filter unit was rinsed with exchange elution buffer (filter sterilized) using the same filter unit (repeating steps 1 and 2).
5. Next, the filter unit was filled with Protein storage Buffer (filter sterilized) and centrifuged at a maximum speed of about 4,800 rpm (3,838×g), using, for example, a Beckman centrifuge GS-15R, swing bucket rotor #S4180. This step was repeated 3 times.
6. Next the concentrated protein sample was removed from the filter unit; collected in the tube (4° C.), and combined with other samples. A 50 of sample was retained for measuring protein concentration.
7. The sample was frozen in liquid nitrogen as 200 mg aliquots.
8. The frozen samples were stored at −80° C.

Calculation of Protein Concentration
Using Absorbance @ A280 nm $$\frac{A280}{a280 \times b}$$

Molecular mass of hCRT is 49142.6 g/L
b=1 cm
a280=82975 for h CRT

Example

Figure 4:
FIG. 4 is a photo of an SDS-PAGE gel of purified human calreticulin (hCRT) samples ranging from 7.5 μg to 30 μg of the protein.

5 µl of sample in 995 µl of Low-Buffer (1:200)
A280 is 0.1256×200=25.12
25.12/82975×1=0.0003027M
0.0003027 M×49142.6(g/L)/1M=14.875 g/L FIG. 4 shows a Coomassie Blue stained gel of purified human calreticulin in the amounts of 7.5 µg, 15 µg and 30 µg of human CRT, purified as described above. The gel shows final purified samples after the two ion chromatography purifications (i.e., Q-Sepharose followed by HRT chromatography) followed by one hydrophobic chromatography purification (ISO chromatography with 20-25% ammonium sulfate elution).

In a preferred embodiment, the two chromatography steps followed by the hydrophobic chromatography step, are performed immediately following one another. However, in certain circumstances it is useful to store a sample (at −20 or other suitable temperature, or even lyophilized (dry powder) after any one of the chromatography steps prior to completing the three step purification of calreticulin. Thus, the present invention encompasses methods where the chromatography steps are performed after storage of an intermediate sample after any one or more of the purifications. Finally, it is contemplated that under certain conditions more than two ion chromatography steps may be desired. Thus, the present invention also encompasses methods where at least two ion chromatography steps are followed by at least one hydrophobic chromatography purification step, to yield a desired purified calreticulin protein product.

In certain embodiments, performing one ion chromatography step followed by one hydrophobic chromatography step will provide a desired purified calreticulin product. In yet additional embodiments, an ammonium sulfate precipitation (20-25%) of E. coli extracted protein followed directly by hydrophobic chromatography will provide a desired purified calreticulin product.

Figure 5:
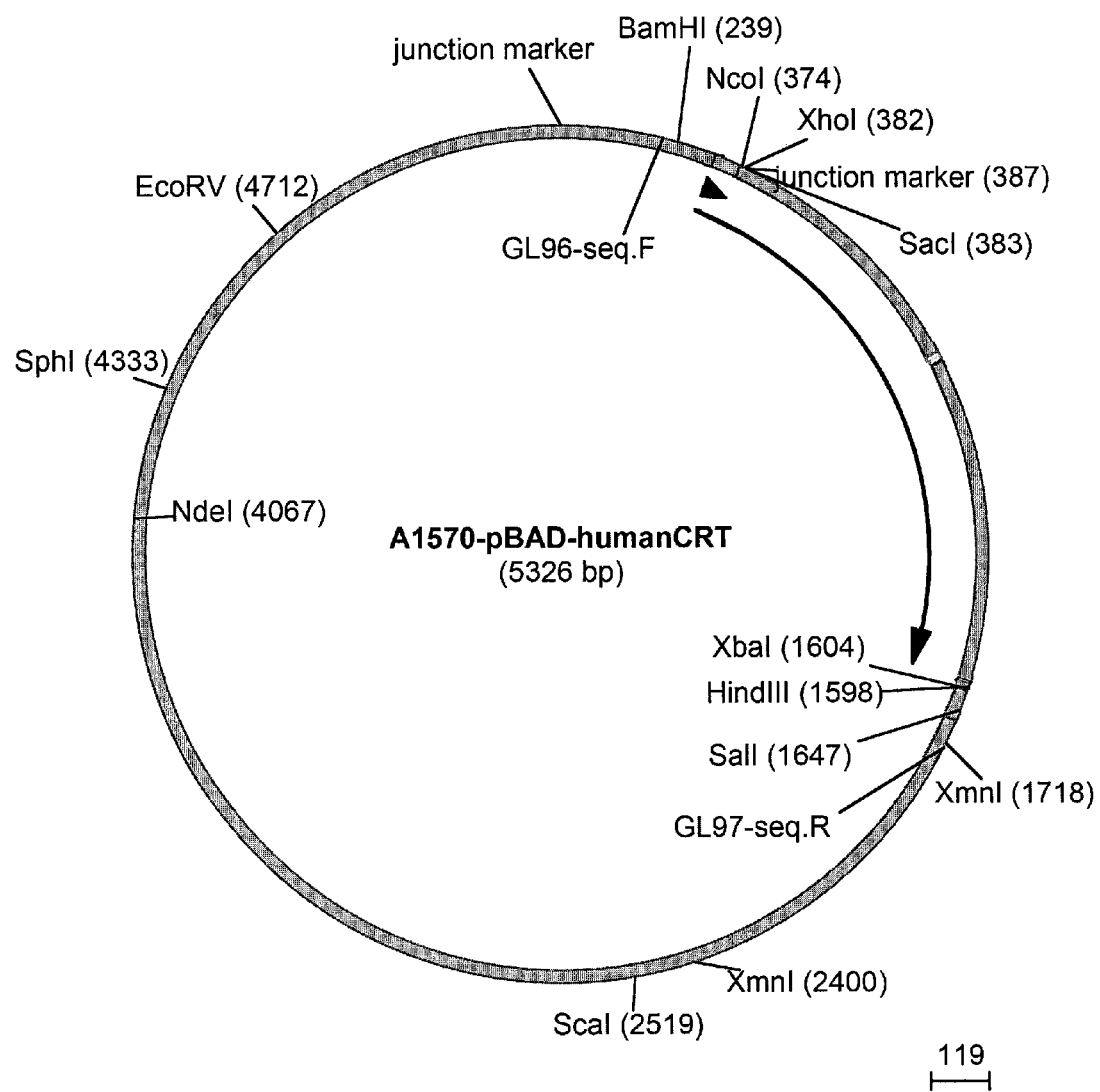
FIG. 5 is a vector map of the 5326 base pair pBAD-hCRT vector.

The Molecular Weight Standards used were the Low range Bio-Rad cat#161-0304:
- →97,400 daltons Phosphorylase b
- →66,200 daltons Serum albumin
- →45,000 daltons Ovalbumin
- →31,000 daltons Carbonic anhydrose
- →21,500 daltons Trypsin inhibitor
- →14,400 daltons Lysozyme FIG. 5 shows a vector map of pBAD/gIII-human CRT. FIG. 6 shows the nucleotide sequence of the pBAD-hCRT plasmid (SEQ ID NO:6) including human calreticulin along with its amino acid sequence (SEQ ID NO:7) including the unique signal sequence from the pBAD construct. In the vector, human calreticulin cDNA was inserted into the EcoR1-Xba1 sites in the multiple cloning site. In a unique feature, the calreticulin cDNA terminates with a stop codon, therefore, c-myc and HIS-tag are not translated but left in the vector. Thus, the calreticulin is secreted and expressed without an affinity tag or label.

Alternatively, removing the nucleotide sequence encoding the HIS and c-myc tag and utilizing the stop codon present in the vector, is another option for eliminating read-through of the vector for producing a non-tagged calreticulin product.

Other features of the vector are as follow (and according to Invitrogen, Carlsbad, Calif.):
 araBAD promoter region: bases 4-276
 Gene III secretion signal: bases 319-373
 rrnB transcriptional termination region: bases 595-752
 Ampicillin resistance gene (ORF): bases 595-752
 pBR322 origin: bases 2037-2710
 AraC ORF: bases 3241-4139.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that values are approximate, and are provided for description.

Patents, patent applications, publications, procedures, and the like are cited throughout this application, the disclosures of which are incorporated herein by reference in their entireties.

What is claimed is:

1. A method for purifying human calreticulin which comprises two sequential ion chromatography purification steps followed by one hydrophobic chromatography purification step utilizing 20-25% ammonium sulfate for elution, wherein said chromatography steps are performed immediately following one another.

2. A method for producing human calreticulin comprising:
   (a) culturing a microorganism having a calreticulin gene under suitable culture conditions;
   (b) inducing expression of the calreticulin gene to produce a calreticulin protein product that is free of an affinity tag or label; and
   (c) purifying the calreticulin product, wherein said calreticulin is purified by the method of claim 1.

3. The method of claim 2, wherein the microorganism is bacteria.

4. The method of claim 3, wherein the bacteria is *Escherichia coli*.

5. The method of claim 2, wherein the calreticulin gene is human calreticulin.

6. The method of claim 2, wherein the calreticulin gene comprises SEQ ID NO: 3.

7. The method of claim 2, wherein the chromatography steps are performed after storage of an intermediate sample after any one or more of the purifications.

8. A method for expressing calreticulin in a prokaryotic cell, which comprises:
   (a) culturing a prokaryotic cell comprising a vector under conditions conducive to gene expression, wherein the vector comprises a nucleic acid encoding calreticulin, an origin of replication, and at least one selectable marker, and wherein the nucleic acid is operatively associated with an expression control sequence;
   (b) inducing expression of the calreticulin gene to produce a calreticulin protein product that is free of an affinity tag or label; and
   (c) purifying said calreticulin protein product using the method of claim 1.

9. The method of claim 8, wherein the prokaryotic cell is *E. coli*.

10. The method of claim 8, wherein the nucleic acid encodes a termination signal.

11. The method of claim 8, wherein the selectable marker is Kanamycin or Ampicillin.

12. A vector comprising an origin of replication, at least one selectable marker, and a multiple cloning site comprising a nucleic acid encoding a signal sequence and calreticulin, and wherein said nucleic acid is operatively associated with an expression control sequence, and wherein said nucleic acid encodes a termination signal and wherein the vector comprises the vector map of FIG. 5, the calreticulin is human calreticulin, the nucleic acid comprises SEQ ID NO:3, and the selectable marker is Kanamycin or Ampillicin.

13. The vector of claim 12, wherein the origin of replication is an *E. coli* origin.

14. A host cell transformed with the vector of claim 12.

* * * * *